United States Patent [19]

Shimizu et al.

[11] Patent Number: 5,543,539

[45] Date of Patent: Aug. 6, 1996

[54] SILACYCLOHEXANE COMPOUND, A METHOD OF PREPARING IT AND A LIQUID CRYSTAL COMPOSITION CONTAINING IT

[75] Inventors: Takaaki Shimizu; Takeshi Kinsho; Tsutomu Ogihara; Tatsushi Kaneko; Ryuichi Saito, all of Niigata-Ken; Hideshi Kurihara, Kawasaki, all of Japan

[73] Assignee: Shin-Etsu Chemical Co., Ltd., Tokyo, Japan

[21] Appl. No.: 388,308

[22] Filed: Feb. 14, 1995

[30] Foreign Application Priority Data

Feb. 17, 1994 [JP] Japan ..................... 6-043181

[51] Int. Cl.$^6$ ..................... C07F 7/08
[52] U.S. Cl. .................. 556/406; 252/299.6; 252/299.63
[58] Field of Search .............. 556/406; 252/299.6, 252/296.63

[56] References Cited

U.S. PATENT DOCUMENTS

| 4,826,984 | 5/1989 | Berlin et al. ............ 556/406 X |
| 4,973,723 | 11/1990 | Cawthon et al. ............ 556/406 |

FOREIGN PATENT DOCUMENTS

| 0276067 | 7/1988 | European Pat. Off. . |
| 0543244 | 5/1993 | European Pat. Off. . |
| 0630903 | 12/1994 | European Pat. Off. . |
| 0632044 | 1/1995 | European Pat. Off. . |

*Primary Examiner*—Paul F. Shaver
*Attorney, Agent, or Firm*—Townsend & Banta

[57] ABSTRACT

There is provided a silacyclohexane compound and method of making same. The silacyclohexane compound has the following formula (1):

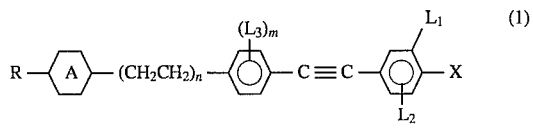

wherein R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8,

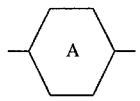

denotes a trans-1-sila-1,4-cyclohexylene or a trans-4-sila-1,4-cyclohexylene group having silicon at positions 1 or 4 with substitutional group(s) of H, F, Cl or $CH_3$; n denotes 0 or 1; $L_1$ and $L_2$ independently denote H, F, Cl, CN or $CH_3$; $L_3$ denotes F; m denotes 0, 1 or 2; and X denotes H, CN, F, Cl, $CF_3$, $CClF_2$, $CHFCl$, $OCClF_2$, $OCHFCl$, $OCHF_2$, $OCF_3$, R or OR group.

6 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the invention

This invention relates to a new silacyclohexane compound, a method of preparing it, and a liquid crystal composition which contains it, as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required in all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and latent liquid crystal compounds. Because of this, it is also important that components of a liquid crystal composition mix easily.

Of these components, the following compounds with the cyclohexyltolane ring structure have been known as compounds which have a high Δn (anisotropy of the refractive index) and a relatively high $T_{NI}$ (nematic-isotropic transition temperature).

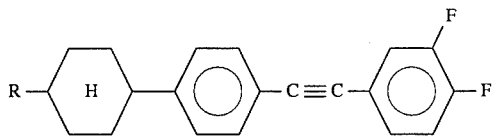

(See Japanese unexamined patent publication Tokkai Sho 63-310838.)

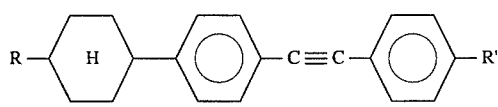

(See Japanese examined patent publication Tokko Sho 64-3852.)

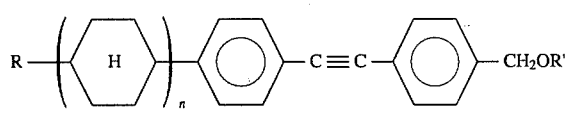

(See Tokko Hei 1-34976.)

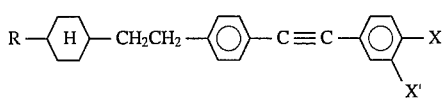

(See Tokko Hei 2-53415.)

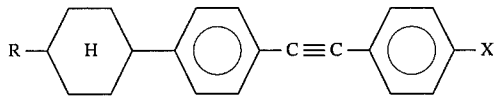

(See Tokko Hei 3-67057.)

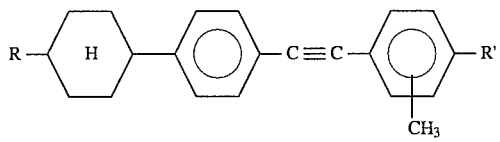

(See Tokko Hei 5-2656.)

The following compounds have been known as compounds which have a high Δn, a relatively high $T_{NI}$ and also a negative Δε (dielectric anisotropy).

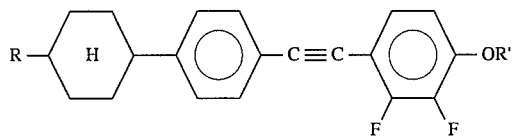

(See Japanese unexamined patent publication Tokuhyo Hei 1-502908.)

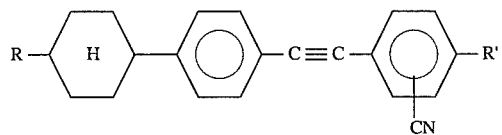

(See Tokkai Hei 3-145450.)

In recent years, along with the expansion of the applications of liquid crystal displays, panel operation modes are diversified and the characteristics required of liquid crystal materials are becoming more and more advanced. The most widely used operation modes are the TN mode with the TFT drive method and the STN mode. Since STN is inexpensive, its display performance is expected to be improved and its applications then widened. There is particularly great demand for faster response time and improved contrast.

One of the ways to shorten the response time is to make the cell gap thinner. In this case, because of the retardation limitation (d×Δn, d: cell gap, Δn: anisotropy of the refractive index), liquid crystal compositions with a larger Δn are required.

In order to obtain a high contrast, a steep threshold characteristic, i.e. a small dielectric constant ratio (Δε/ε, Δε: dielectric anisotropy, ε: dielectric constant along the minor axis) is required. Most of the liquid crystal compounds have a positive or near-zero Δε, and therefore a liquid crystal compound with a negative Δε is required to decrease the dielectric constant ratio of mixed compositions using them.

BRIEF SUMMARY OF THE INVENTION

The object of this invention is to provide a conventionally unknown and completely new liquid crystal compound with a large Δn containing silacyclohexane rings with a silicon atom(s) in its molecular structure for use as a component of a liquid crystal composition, wherein those with a benzene ring(s) with lateral fluorine substitution or nitrile group substitution,

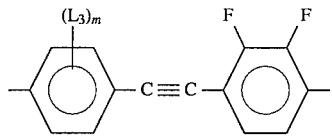

and

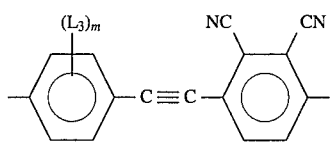

for example, have an effect of decreasing Δε.

This invention provides a silacyclohexane compound represented by the following general formula (I).

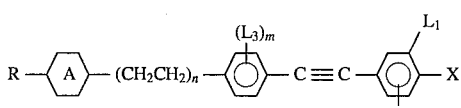

In this formula, R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

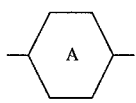

denotes a trans-1-sila-1,4-cyclohexylene or trans-4-sila-1,4-cyclohexylene group whose silicon at position 1 or position 4 has a substitutional group(s) of H, F, Cl or $CH_3$. n denotes 0 or 1. $L_1$ and $L_2$ independently denote H, F, Cl, CN or $CH_3$. $L_3$ denotes F. m denotes 0, 1 or 2. X denotes CN, F, Cl, $CF_3$, $CClF_2$, CHFCl, $OCClF_2$, OCHFCl, $OCHF_2$, $OCF_3$, R or OR group.

This invention also provides a method of preparing the silacyclohexane compound represented by the general formula (1) characterized by the use of a carbon-carbon bond formation reaction using dehydrohalogenation (HQ) in the presence of a palladium catalyst between an aromatic halide

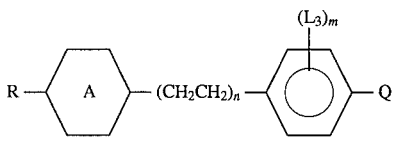

(Q denotes a halogen atom) and a substituted acetylene compound

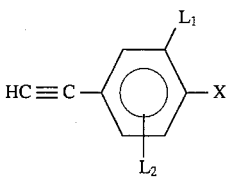

This invention also provides a method of preparing the silacyclohexane compound represented by the general formula (1) characterized by the use of a carbon-carbon bond formation reaction using dehydrohalogenation (HQ) in the presence of a palladium catalyst between an aromatic halide

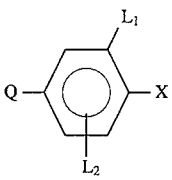

and a substituted acetylene compound

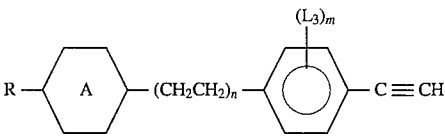

This invention also provides a method of preparing the silacyclohexane compound represented by the general formula (1) characterized by the use of a carbon-carbon bond formation reaction using demetallichalogenation (MQ) in the presence of a palladium catalyst or nickel catalyst between an aromatic halide

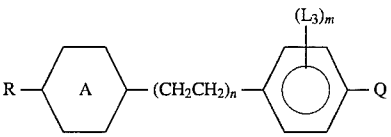

and an alkynyl metal reagent

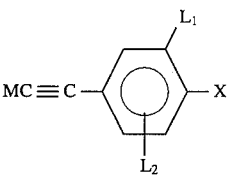

(M denotes Cu, MgP (P denotes a halogen atom) or ZnP).

This invention also provides a method of preparing the silacyclohexane compound represented by the general formula (1) characterized by the use of a carbon-carbon bond formation reaction using demetallichalogenation (MQ) in the presence of a palladium catalyst or nickel catalyst between an aromatic halide

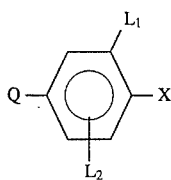

and an alkynyl metal reagent

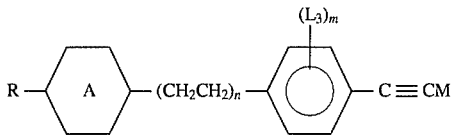

This invention also provides a liquid crystal composition characterized by containing the silacyclohexane compound represented by the general formula (1) and a liquid crystal display device characterized by containing this liquid crystal composition.

DETAILED DESCRIPTION

This invention is described in detail below.

First, specific examples of the silacyclohexane compound represented by the general formula (I) are described.

The new ring structures of this invention are the following ring structures containing a trans-1- or trans-4-silacyclohexane ring.

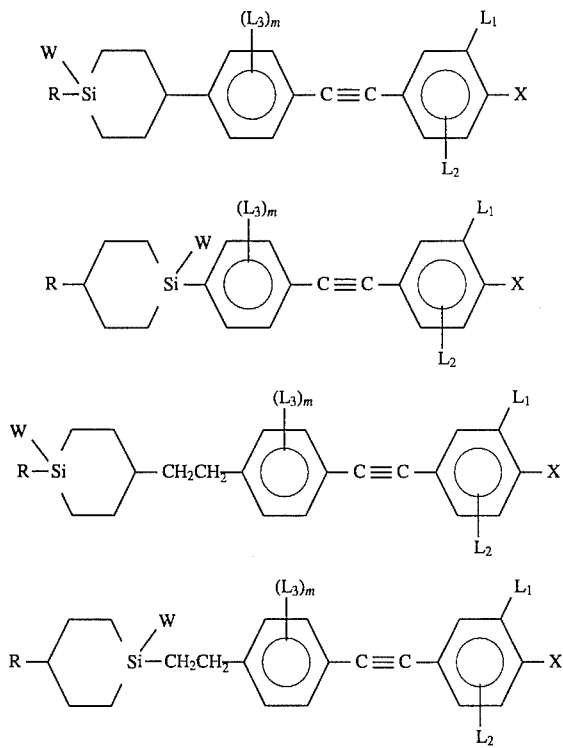

R denotes the following groups listed in (a) through (e):

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1difluoroheptyl, 1,1-difluorooctyl, 1,1-difluorononyl, 1,1-difluorodecyl, 2,2-difluoroetyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-diflouoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl or 10,10-difluorodecyl group (c) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (d) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl or ethoxypentyl group (e) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W denotes a H, F, Cl or $CH_3$ group.

$L_1$ and $L_2$ independently denote a H, F, CN, Cl or $CH_3$ group. $L_3$ denotes F. m denotes 0, 1 or 2.

X denotes H, CN, hydrogen, F, Cl, or a $CF_3$, $CClF_2$, $OCClF_2$, $OCHFCl$, $OCHF_2$, $OCF_3$, R or OR group.

Specific examples of the partial structure
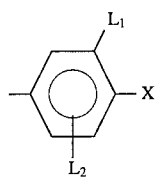
follow.
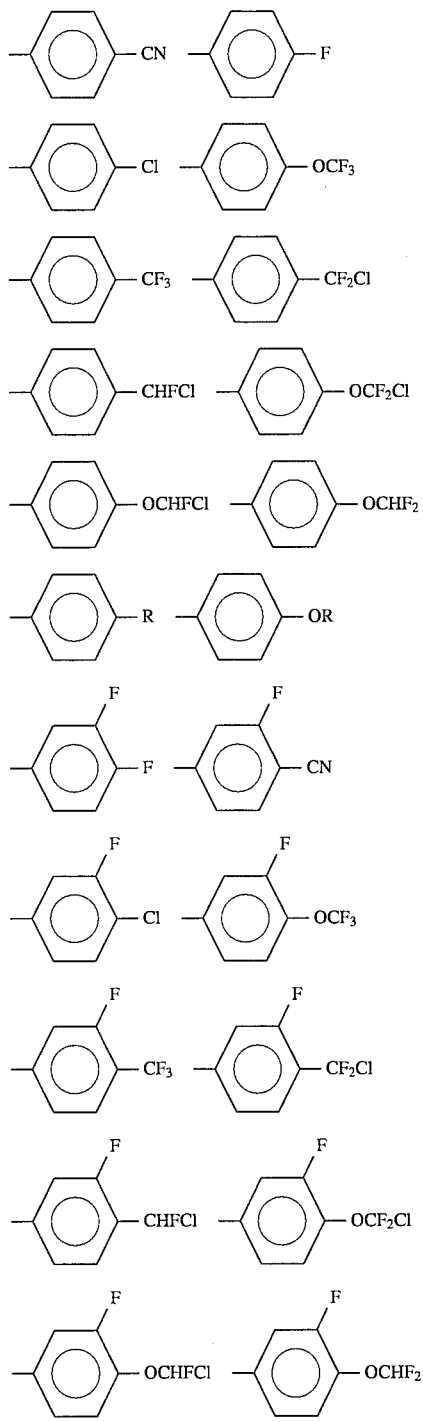
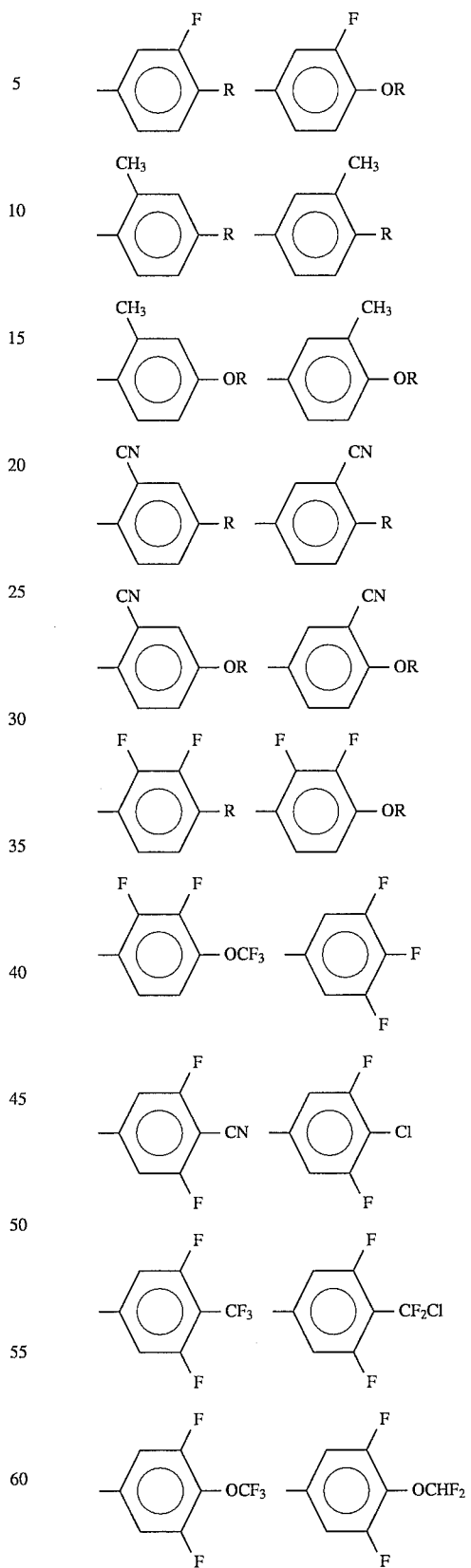

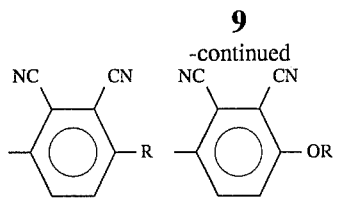

Of these, the following are desirable for practical use. For the ring structure,

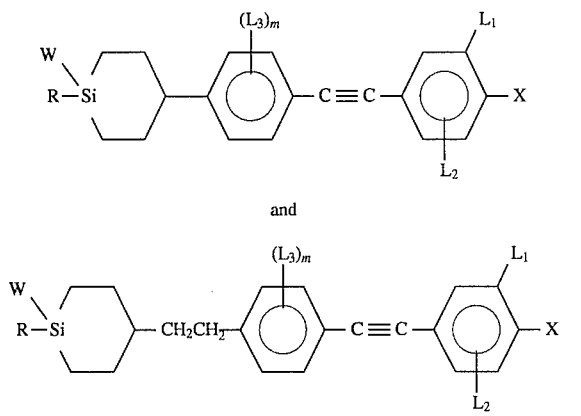

are desirable.

For R, the following groups listed in (i) through (m) are preferable:

(i) A linear-chain alkyl group with a carbon number of 2–7, i.e. an ethyl, n-propyl, n-butyl, n-pentyl, n-hexyl or n-heptyl group (j) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups (k) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (l) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (m) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and $CH_3$ groups are desirable for W in practical use. For

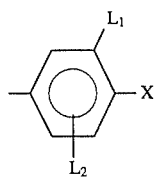

the following are desirable.

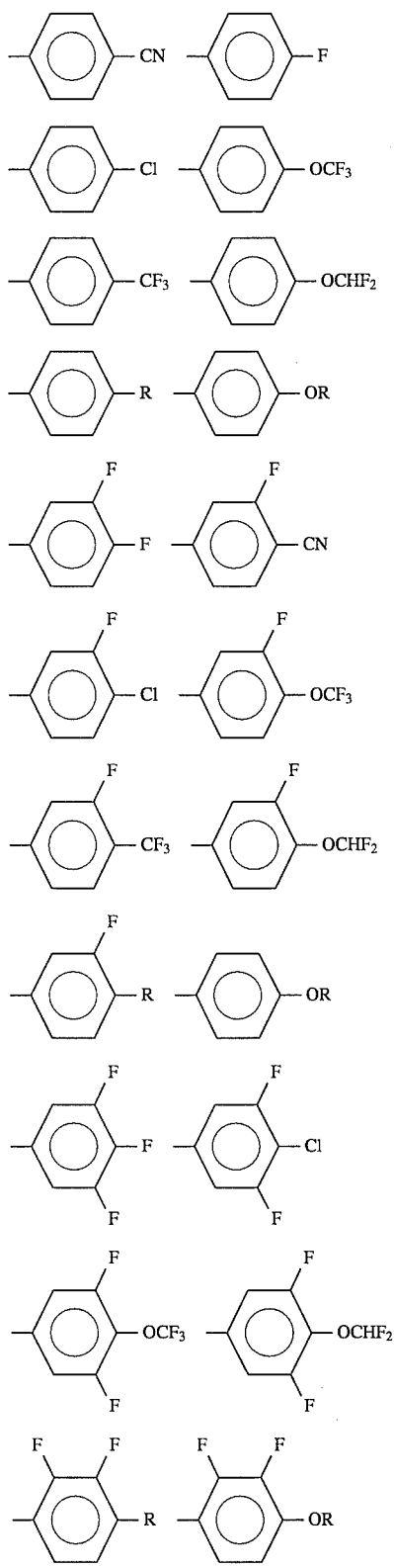

The manufacturing methods of these compounds are described next.

These compounds are prepared by a carbon-carbon bond formation reaction using dehydrohalogenation between an aromatic halide and a substituted acetylene compound or a carbon-carbon bond formation reaction using demetallichalogenation between an aromatic halide and an alkynyl metal reagent. A detailed description is given below.

In the reaction between the aromatic halide

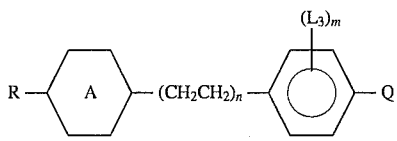

and the substituted acetylene compound

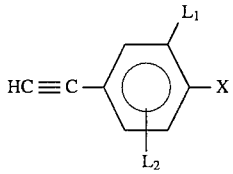

or the reaction between the aromatic halide

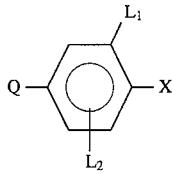

and the substituted acetylene compound

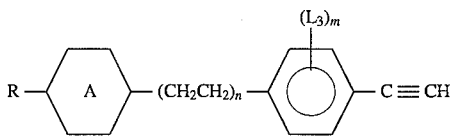

the coupling reaction by means of dehydrohalogenation proceeds by using an organic base in the presence of a palladium catalyst.

The reaction proceeds even more easily when a copper compound coexists as an additional catalyst.

Examples of the palladium catalysts include divalent or zero-valent palladium compounds. Particularly preferable are palladium (II) acetate and palladium (II) chloride, as well as compounds comprising these and ligands, such as bis (triphenylphosphine) palladium (II) acetate, bis (triphenylphosphine) palladium (II) chloride, bis (acetonitrile) palladium (II) acetate, bis (acetonitrile) palladium (II) chloride and (1,5-cyclooctadiene) palladium (II) chloride, and also tetrakis (triphenylphosphine) palladium (0).

Examples of the copper catalyst include monovalent or divalent copper halides and acetates, among which copper (I) iodide is a particularly good catalyst.

Preferable examples of the organic base include triethylamine, diethylamine, tri-n-butylamine, di-n-butylamine, butylamine, triisopropylamine, diisopropylamine, dimethylamine, isopropylethylamine and tetra-n-butylammonium iodide. These bases can be used as a solvent in an excessive amount, or 1–5 equivalents of the amount of the hydrogen halide to be produced can be added to another solvent.

In the reaction between the aromatic halide

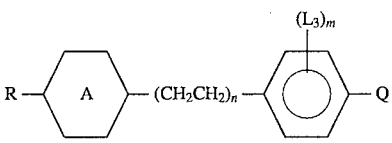

and the alkynyl metal reagent

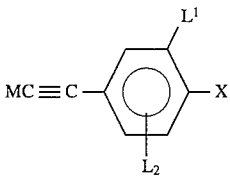

or the reaction between the aromatic halide

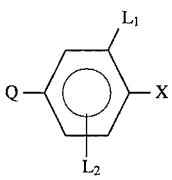

and the alkynyl metal reagent

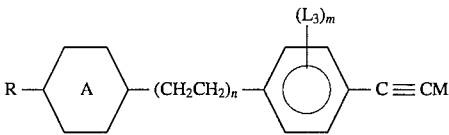

the coupling reaction by means of demetallichalogenation proceeds in the presence of a palladium catalyst or a nickel catalyst.

Examples of the palladium catalyst include divalent or zero-valent palladium compounds. Particularly preferable are palladium (II) acetate and palladium (II) chloride, as well as compounds comprising these and ligands, such as bis (triphenylphosphine) palladium (II) acetate, bis (triphenylphosphine) palladium (II) chloride, bis (acetonitrile) palladium (II) acetate, bis (acetonitrile) palladium (II) chloride and (1, 5-cyclooctadiene) palladium (II) chloride, and also tetrakis (triphenylphosphine) palladium (0).

Preferable examples of the nickel catalyst include (1,3-bis (diphenylphosphino) propane) nickel (II) chloride, (1,2-bis (diphenylphosphino) ethane) nickel chloride, bis (triphenylphosphine) nickel chloride and tetrakis (triphenylphosphine) nickel (0).

Following a conventional after treatment, the product synthesized as described above can be purified by means of recrystallization, chromatography or other conventional purification processes to obtain the target silacyclohexane compound with a high purity.

Known compounds used for mixing with the silacyclohexane compound of this invention to obtain the liquid crystal compound can be chosen from the following listed below:

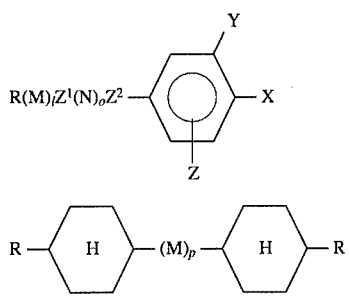

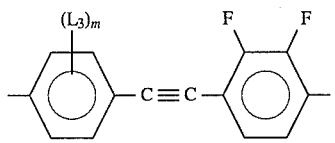

and

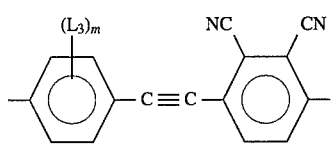

In the above formulas, (M) and (N) denote one of the following items 1) through 5):
1) A trans-1,4-cyclohexylene group which has no substitution or which has one or more substitutional groups such as F, Cl, Br, CN or alkyl groups
2) A trans-1,4-cyclohexylene group that has 0 or S substituted for one or nonadjacent two CH2 groups in the cyclohexane ring
3) A 1,4-cyclohexenylene group
4) A 1,4-phenylene group which has no substitution or which has one or two substitutional groups such as F, Cl, $CH_3$ or CN groups
5) A 1,4-phenylene group that has an N atom substituted for one or two CH groups in the ring.

$Z^1$ and $Z^2$ each denote —$CH_2CH_2$—, —CH=CH—, —C≡C—, —$CO_2$—, —OCO—, —$CH_2O$—, —$OCH_2$— or a single bond.

l, o=0, 1 or 2 (where l+o=1, 2 or 3), and p=0, 1 or 2.

R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

X denotes H, CN, F, Cl, $OCF_3$, $OCHF_2$, $CF_3$, $CClF_2$, CHFCl, $OCClF_2$, OCHFCl, R or OR group.

Y denotes H or F. Z denotes H or F.

In the above description, if l=2 and p=2, then (M) can contain heterogeneous rings, and if o=2, then (N) can contain heterogeneous rings.

The ratio of one or more types of the silacyclohexane compound of this invention contained in the liquid crystal composition is 1–50 wt. %, more preferably 5–30 wt. %. The liquid crystal composition can also contain a polygenetic dye(s) to generate a colored guest-host system and additives to change the dielectric anisotropy, viscosity and the orientation of the nematic phase.

The liquid crystal phase thus formed is sealed between transparent base plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the guest-host (GH) method and the polymer dispersion (PDLC) method can be adopted.

As described thus far, the compound of this invention provides a conventionally unknown and completely new liquid crystal compound with a large Δn containing silacyclohexane rings with a silicon atom(s) in its molecular structure for use as a component of a liquid crystal composition, wherein those with a benzene ring(s) with lateral fluorine substitution or nitrile group substitution, for example, have an effect of decreasing Δε.

EXAMPLE

The details of this invention are described below by referring to specific examples.

Example 1

Preparation of 4-(trans-4-n-propyl-4-silacyclohexyl) -4'-methoxytolane

The reaction mixture prepared by adding 50 mg of copper (I) iodide and 100 mg of bis (triphenylphosphine) palladium (II) chloride to a mixture of 3.44 g (10.0 mmol) of trans-4-(p-iodophenyl)- 1-n-propyl-1-silacyclohexane, 13.5 g (10.2 mmol) of p-methoxyphenylacetylene and 50 ml of diethylamine was refluxed for 8 hours as it was stirred. After a conventional after treatment, purification was conducted by means of silica-gel column chromatography to obtain 2.79 g (yield 80%) of the target product.

IR (KBr table method): 2954, 2916, 2866, 2214, 2102, 1603, 1516, 1286, 1250, 1174, 1028, 984, 887, 831 and 814 [$cm^{-1}$]

Transition temperatures: C-N: 82.5° C., N-I: 195.7° C.

The following compounds shown in Examples 2–5 were obtained in the same manner as Example 1.

Example 2

4-(trans-4-n-propyl-4-silacyclohexyl)-3', 4'-difluorotolane

IR (KBr table method): 2955, 2916, 2872, 2848, 2216, 2114, 1599, 1518, 1419, 1267, 984, 876, 825 and 769 [$cm^{-1}$]

Transition temperatures: C-N: 58.0° C., N-I: 113.2° C.

Example 3

4-(trans-4-n-ethenyl-l-silacyclohexyl)-3', 4'-difluorotolane

Example 4

4-(trans-4-(3-methoxypropyl)-1-silacyclohexyl)-4'-fluorotolane

Example 5

Preparation of 4-(trans-4-n-propyl-4-silacyclohexyl)-4'-ethyltolane 100 mg of tetrakis (triphenylphosphine) palladium (0) and 50 mg of copper (I) iodide were added to a mixture of 1.21 g (5.00 mmol) of trans-4-(p-ethynylphenyl)-1-n-propyl-1-silacyclohexane, 1.50 g (6.46 mmol) of p-iodoethylbenzene and 30 ml of triethylamine. The reaction mixture was stirred for 20 hours at room temperature. After a conventional after treatment, purification was conducted by means of silica-gel column chromatography to obtain 1.30 g (yield 75%) of the target product.

The following compounds shown in Examples 6–8 were obtained in the same manner as Example 5.

Example 6

4-(trans-4-n-propyl-4-silacyclohexyl)-4'-trifluoromethoxytolane

Example 7

4-(trans-4-n-propyl-4-silacyclohexyl)-2',4'-dimethyltolane

Example 8

4-(trans-4-isopenty-1-methy-1-silacyclohexyl)-4'-methoxymethyltolane

Example 9

Preparation of 4-(trans-4-n-propyl-4-silacyclohexyl) -4'-ethoxy-2',3'-difluorotolane 10.0 ml (10.0 mmol) of a tetrahydrofuran solution of 1.0M 4-(trans-4-n-propyl-4-silacyclohexyl) phenylethyl zinc chloride was dripped into a mixture of 4.20 g (14.8 mmol) of 2,3-difluoro-4-iodoethoxybenzene, 70 mg of tetrakis (triphenylphosphine) palladium (0) and 15 ml of tetrahydrofuran. The reaction mixture was reacted for 2 hours at 50° C. After a conventional after treatment, purification was conducted by means of silica-gel column chromatography to obtain 3.25 g (yield 88%) of the target product.

The following compounds shown in Examples 10–12 [11?]were obtained in the same manner as Example 9.

Example 10

4-( trans-4-n-propyl-4-silacyclohexyl )-4'-fluorotolane

Example 11

4-(trans-4-n-propyl-4-silacyclohexyl )-4 '-cyanotolane

Example 12

Preparation of 4-(2-(trans-4-n-propyl-4-silacyclohexyl) ethyl)-4'-fluorotolane 20.0 ml (30.0 mmol) of a tetrahydrofuran solution of 1.5M p-fluorophenylethynyl magnesium chloride was dripped into a mixture of 3.50 g (10.8 mmol) of 4-(2-(p-bromophenyl) ethyl)-1-n-propyl-1-silacyclohexane, 80 mg of tetrakis (triphenylphosphine) palladium (0) and 20 ml of tetrahydrofuran. The reaction mixture was stirred for 8 hours at room temperature. After a conventional after treatment, purification was conducted by means of silica-gel column chromatography to obtain 2.87 g (yield 73%) of the target product.

The following compounds shown in Examples 13–16 were obtained in the same manner as Example 12.

Example 13

4-(2-( trans-4-ethyl-4-silacyclohexyl ) ethyl )-4'-n-butyl tolane

Example 14

2-fluoro-4-(trans-4-n-propyl-4-silacyclohexyl)-4'-fluorotolane

Example 15

2-fluoro-4-(trans-4-n-propyl-4-silacyclohexyl)-3',4'-difluorotolane

Example 16

4-(2-(trans-4-n-propyl-4-silacyclohexyl) ethyl)-3',4'-difluorotolane

Example 17

A liquid crystal mixture A comprising 20% of trans-4-(2-(3,4-difluorophenyl) ethyl)-1-butylcyclohexane, 32% of 4-(trans-4-(trans-4-ethylcyclohexyl) cyclohexyl)-1,2-difluorobenzene, 28% of 4-(trans-4-(trans-4-n-propylcyclohexyl) cyclohexyl)1,2-difluorobenzene and 20% of 4-(trans-4-(trans-4-n-pentylcyclohexyl) cyclohexyl)-1,2-difluorobenzene exhibits the following characteristics:

$T_{NI}$ (nematic-isotropic transition temperature)=75° C.

$\Delta n$ (double refraction index at 589 nm and 20° C.)=0.0720

A mixture comprising 85% of this mixture and 15% of the 4-(trans-4-n-propyl-4-silacyclohexyl)-4'-methoxytolane obtained in Example 1 exhibited an increase in both $T_{NI}$ and $\Delta n$, as shown below.

$T_{NI}$=93° C.

$\Delta n$=0.0950

Example 18

A mixture comprising 85% of the mixture of Example 17 and the 4-(trans-4-n-propyl-4-silacyclohexyl)-4'-ethoxy-2',3'-difluorotolane obtained in Example 9 exhibited an increase in $T_{NI}$ and a decrease in $\Delta\epsilon$ (dielectric anisotropy), as shown in Table 1 below.

TABLE 1

|  | Mixture A | The mixture containing the silacyclohexane compound of Example 9 |
|---|---|---|
| $T_{Ni}$ | 75° C. | 91° C. |
| $\Delta\epsilon$ (1KHz, 20° C.) | 4.20 | 3.05 |

We claim:

1. A silacyclohexane compound represented by the following formula (1):

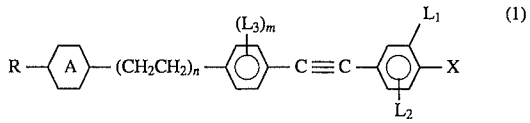

wherein R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8,

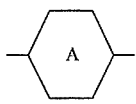

denotes a trans-1-sila-1,4-cyclohexylene or a trans-4-sila-1,4-cyclohexylene group having silicon at positions 1 or 4 with substitutional group(s) of H, F, Cl or $CH_3$; n denotes 0 or 1; $L_1$ and $L_2$ independently denote H,F, Cl, CN or $CH_3$; $L_3$ denotes F; m denotes 0, 1 or 2; and X denotes H, CN, F, Cl, $CF_3$, $CClF_2$, $CHFCl$, $OCClF_2$, $OCHFCl$, $OCHF_2OCF_3$, R or OR group.

2. A method of preparing the silacyclohexane compound of claim 1, comprising reacting in the presence of a palladium catalyst an aromatic halide having the formula:

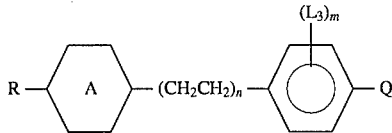

wherein Q denotes a halogen atom with a substituted acetylene compound having the formula:

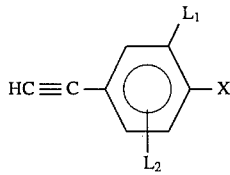

3. A method of preparing the silacyclohexane compound of claim 1, comprising reacting in the presence of a palladium catalyst an aromatic halide having the formula:

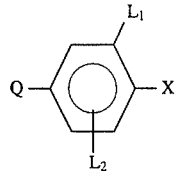

with a substituted acetylene compound having the formula:

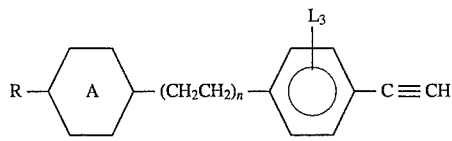

4. A method of preparing the silacyclohexane compound of claim 1, comprising reacting in the presence of a palladium or nickel catalyst an aromatic halide having the formula:

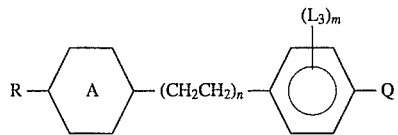

with an alkynyl metal reagent having the formula:

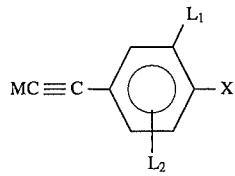

wherein M denotes Cu, MgP (P denotes a halogen atom) or ZnP.

5. A method of preparing the silacyclohexane compound of claim 1, comprising reacting in the presence of a palladium or nickel catalyst an aromatic halide having the formula:

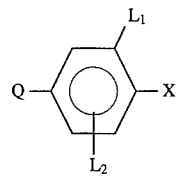

with an alkynyl metal reagent having the formula:

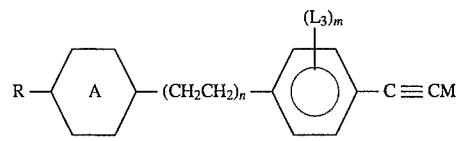

wherein M denotes Cu, MgP, (P denotes a halogen atom) or ZnP.

6. A liquid crystal composition comprising the silacyclohexane compound of claim 1.

* * * * *